United States Patent [19]

Mellul et al.

[11] Patent Number: 5,851,539

[45] Date of Patent: *Dec. 22, 1998

[54] FLUOROCARBON CONTINUOUS PHASE WATER-IN-OIL EMULSIONS EMPLOYING SILICONE SURFACTANTS

[75] Inventors: Myriam Mellul, L'Hay les Roses; Pascal Arnaud, Creteil, both of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 736,491

[22] Filed: Oct. 24, 1996

Related U.S. Application Data

[63] Continuation of Ser. No. 139,163, Oct. 21, 1993, abandoned.

[30] Foreign Application Priority Data

Oct. 21, 1992 [FR] France .................................. 92 12608

[51] Int. Cl.⁶ .............................. A61K 7/00; A61K 7/021
[52] U.S. Cl. .............................. 424/401; 424/62; 424/63; 424/59; 424/70.1; 252/309
[58] Field of Search ......................... 252/309; 424/70.12, 424/70.31, 401, 63, 673, 59, 70.1, 62; 514/975, 937, 63

[56] References Cited

U.S. PATENT DOCUMENTS

| | | | |
|---|---|---|---|
| 3,792,977 | 2/1974 | Guenthner | 8/615 |
| 3,993,744 | 11/1976 | Cella et al. | 424/70 |
| 4,065,259 | 12/1977 | Jackson | 8/615 |
| 4,122,029 | 10/1978 | Gee et al. | 252/309 |
| 4,304,563 | 12/1981 | Grollier et al. | 8/127.51 |
| 4,311,695 | 1/1982 | Starch | 514/63 |
| 4,803,067 | 2/1989 | Brunetta et al. | 424/63 |
| 4,960,764 | 10/1990 | Figueroa. Jr. et al. | 514/63 |
| 5,036,108 | 7/1991 | Asahi et al. | 514/937 |
| 5,183,588 | 2/1993 | Salerno et al. | 252/312 |
| 5,216,033 | 6/1993 | Pereira et al. | 424/63 |
| 5,256,422 | 10/1993 | Albert et al. | 514/937 |
| 5,304,334 | 4/1994 | Lahanas et al. | 242/309 |
| 5,362,482 | 11/1994 | Yoneyama et al. | 424/63 |
| 5,368,847 | 11/1994 | Brunetta et al. | 424/401 |
| 5,380,455 | 1/1995 | Tsuda et al. | 252/174.23 |
| 5,496,866 | 3/1996 | Sommerfeld et al. | 521/131 |

FOREIGN PATENT DOCUMENTS

| | | |
|---|---|---|
| 0 051 526 | 5/1982 | European Pat. Off. . |
| 0 296 661 | 12/1988 | European Pat. Off. . |
| 0 390 206 | 10/1990 | European Pat. Off. . |
| 0 422 984 | 4/1991 | European Pat. Off. . |
| 0 494 412 | 7/1992 | European Pat. Off. . |
| 2 450 105 | 9/1980 | France . |
| 2 087 882 | 6/1982 | United Kingdom . |
| WO88/06434 | 9/1988 | WIPO . |
| WOA9311103 | 10/1993 | WIPO . |

*Primary Examiner*—Richard D. Lovering
*Assistant Examiner*—Daniel S. Metzmaier
*Attorney, Agent, or Firm*—Jacobson, Price, Holman & Stern, PLLC

[57] ABSTRACT

The present invention relates to a W/O type emulsions comprising an aqueous phase emulsified by means of a silicone surfactant, in a continuous phase containing at least one fluorohydrocarbon. It also relates to the use of certain silicone surfactants for the preparation of such emulsions. Said emulsions have utility in cosmetics and dermatology.

11 Claims, No Drawings

FLUOROCARBON CONTINUOUS PHASE WATER-IN-OIL EMULSIONS EMPLOYING SILICONE SURFACTANTS

This application is a continuation of application Ser. No. 08/139,163, filed Oct. 21, 1993, now abandoned.

The present invention relates to emulsions containing an aqueous phase in a fluorohydrocarbon continuous phase, their preparations as well as their uses in the fields of cosmetics and dermatology.

In the cosmetic field in particular, the water-in-oil W/O emulsions are commonly used since they make it possible to form, at the surface of the skin, a film which prevents the loss of transepidermal water and protects the skin from external damage. Given the demands of consumers with respect to this type of emulsions which must have, at the same time, a good cosmetic quality which manifests itself in terms of appearance, texture and ease of application, good protective properties, a good preservation of the efficacy over time (cosmetic behaviour) which presuppose, on the part of the film, a high water-repelling power, as well as a good resistance to sweat and sebum, it is highly advantageous to be able to obtain emulsions exhibiting all these properties without exhibiting the disadvantages of conventional W/O emulsions.

Indeed, the W/O emulsions prepared from conventional hydrocarbon oils or from silicone oils generally have the disadvantage of a heavy, greasy and/or sticky texture and a poor cosmetic behaviour.

Thus, when silicone oils are used in the continuous phase, while the cosmeticity is enhanced, the resistance to sebum remains poor.

Moreover, for the abovementioned conventional oils, the substitution of hydrogen atoms by fluorine atoms brings about an enhancement of the hydrophobic, film-forming and lubricating properties as well as a certain lipophobicity. The presence of fluorine atom was also known to induce a decrease in the solubility properties for the raw materials customarily used in cosmetics.

In order to prepare W/O emulsions, various types of fluorinated oils and especially the perfluorinated oils where all the hydrogen atoms are substituted by fluorine atoms, such as perfluoropolyethers and perfluoro-alkanes, the fluorinated silicones where a fraction of the alkyl groups carried by the silicone skeleton is fluorinated, have therefore already been proposed for the continuous phase. However, none of these types of fluorinated oil has been able, up until now, to lead to suitable emulsions.

Thus, a first possibility of formulation of perfluorinated oils in W/O systems consists in dispersing them, either in the conventional W/O emulsions as described by Patents EP 196,904 and EP 358,528, or in silicone emulsions as claimed by Patent FR 2,653,125. However, their total insolubility (except in certain fluorinated solvents) may result in non-homogeneous distributions of these oils in the preparations, bringing about a decrease in the performance of the products.

Moreover, their emulsification in the form of a perfluorinated W/O system by hydrocarbon surfactants results most often in very unstable emulsions, except in specific cases where the fluorinated oil is a chlorofluorocarbon of low boiling point as described by Patents U.S. Pat. No. 3,502,586 and JP 61-108699 and on the condition that the water content remains low.

These last two patents do not, in addition, relate to the cosmetic field. Fluorinated surfactants make it possible, on the other hand, to obtain stable perfluorinated W/O type emulsions and microemulsions as described by Patents FR 2,184,786, EP 250766 and EP 315841 and FR 2,630,347, but the use of this type of surfactants remains limited in cosmetics.

As regards the fluorinated silicones, they have also been proposed for the preparation of fluorinated silicone W/O emulsions as described in Patents JP 2-298338 and JP 2-295912. But, as in the case of the perfluorinated oils, the presence of fluorinated groups in the silicone skeleton induces a substantial reduction in the solubility properties with conventional cosmetic compounds.

In contrast to the preceding two classes of oils, fluorohydrocarbons have the advantage of being compatible with the raw materials commonly used in cosmetics, in particular the hydrocarbon oils and the silicone oils.

Given this compatibility, it proved very useful to be able to emulsify the fluorohydrocarbons in order to obtain W/O systems which would meet all the criteria stated above while being easy to formulate.

The Applicant has now been able to produce W/O emulsions in which the aqueous phase is emulsified in a continuous phase consisting of at least one fluorohydrocarbon. The aqueous phase is emulsified by means of a silicone surfactant.

Thus, the present invention relates to a W/O type emulsion consisting of an aqueous phase emulsified by means of a silicone surfactant, in a continuous phase containing a fluorohydrocarbon.

The term fluorohydrocarbon designates compounds whose chemical structure contains a carbon skeleton in which some hydrogen atoms have been substituted by fluorine atoms.

For the fluorohydrocarbons, the rate of substitution of hydrogen atoms by fluorine atoms is defined in the form of the ratio: number of fluorine atoms/(number of fluorine atoms+number of hydrogen atoms) where only the hydrogen atoms linked to the carbon atoms of the skeleton are taken into account. The fluorohydrocarbons or fluorohydrocarbon oils of the invention contain at least one hydrocarbon group in the molecule.

According to the invention, by using silicone surfactants, it is possible to emulsify fluorohydrocarbon oils and to obtain stable emulsions with fluorohydrocarbon oils whose fluorine atom level is unimportant.

The formula for the fluorohydrocarbons of the invention is the following formula I:

$$(R_F)_x-(A)_y-(R_H)_z \qquad (I)$$

in which:

x represents 1, 2 or 3, y represents 0 or 1, z represents 0, 1, 2 or 3, on the condition that y and z are not simultaneously 0, and that when z is 0, x is 2 or 3, $R_F$ represents a saturated or unsaturated, aliphatic or aromatic fluorinated radical with a linear, branched or cyclic chain, it being possible for this chain to be functionalized and/or to be interrupted by divalent atoms such as oxygen or sulphur, or trivalent atoms such as nitrogen and/or substituted by hydrogen atoms or other halogen atoms, on the condition that, for two carbon atoms of the skeleton, not more than one of these substituents other than fluorine is present, $R_H$ represents a saturated or unsaturated, aliphatic or aromatic hydrocarbon radical with a linear, branched or cyclic chain, it being possible for this chain to be functionalized and/or interrupted by one or more divalent atoms such as oxygen or sulphur or by one or more trivalent atoms such as nitrogen, A represents a di-, tri- or quadrivalent radical such as $$\diagdown C \diagup, \diagdown CH-, -N \diagup, -CO-N \diagup, -SO_2N \diagup,$$

$$-O-\underset{\underset{O}{|}}{\overset{\overset{O}{||}}{P}}-O-$$

cyclic, aliphatic or aromatic structures or ethylenic unsaturations.

Functionalized is understood to mean, according to the invention, an inserted, terminal or pendent substitution of the skeleton by at least one functional organic group such as an alcohol, thiol, acid, carbonyl, sulphoxide, ester, amide, amine, phosphate, ethylene, acetylene, and enamine or sulphonamide functional group.

Ethylenic unsaturation is understood to mean for example $$\diagdown C=C \diagup, \diagdown C=CH- \text{ or } -CH=CH-.$$

Preferably, $R_H$ represents a linear or branched $C_1$–$C_{22}$ alkyl radical or a mixture of linear or branched $C_1$–$C_{22}$ alkyl radicals, a $C_6$–$C_{10}$ aryl radical or a $C_7$–$C_{15}$ aralkyl radical.

Preferably $R_F$ represents a perfluoroalkyl radical having 4 to 22 carbon atoms.

According to the invention, the fluorohydrocarbons used preferably have a substitution rate of between 0.5 and 95%. Preferably, this rate is greater than 10% and less than 80%.

By way of illustration, there may be mentioned the compounds possessing perfluorocarbon groups and hydrocarbon groups, the total number of carbon being between 10 and 30, the number of carbon atoms of the hydrocarbon groups being equal to or greater than twice the number of carbon atoms of the perfluorocarbon groups, as described in the document JP 63-002916.

Similarly, by way of illustration, there may be mentioned the fluorohydrocarbons whose general structure is defined by the formula (III).

$$R_1-(CH_2)_n-X-[C_3H_5(OH)]-(Y)_x-R_2 \quad (III)$$

where $C_3H_5(OH)$ represents:

$$-CH_2-\underset{\underset{CH_2OH}{\overset{|}{OH}}}{CH}-CH_2- \quad \text{or} \quad -\underset{\underset{CH_2OH}{|}}{CH}-CH_2- \quad \text{or}$$

$$-CH_2-\underset{\underset{CH_2OH}{|}}{CH}-$$

$R_1$ represents a linear or branched perfluorinated $C_4$–$C_{20}$ alkyl radical or a mixture of linear or branched perfluorinated $C_4$–$C_{20}$ radicals, $R_2$ represents a linear or branched $C_1$–$C_{22}$ alkyl radical or a mixture of linear or branched $C_1$–$C_{22}$ alkyl radicals or a $C_6$–$C_{10}$ aryl or $C_7$–$C_{15}$ aralkyl radical, X and Y, which are identical or different, represent:

$$-O-, \quad -S-, \quad -\overset{\overset{O}{\uparrow}}{S}-, \quad \text{or} \quad -\overset{\overset{O \diagdown \diagup O}{\diagdown \diagup}}{S}-;$$

provided that X and Y do not simultaneously represent $$-\overset{\overset{O}{\uparrow}}{S}- \quad \text{or} \quad -\overset{\overset{O \diagdown \diagup O}{\diagdown \diagup}}{S}-,$$

n is between 0 and 4, and
x represents 0 or 1.

These compounds which are used according to the invention are described in FR-A-WO 93/11103 and EP-A-166,696.

Moreover, there may also be used according to the invention the compounds of formula (IV):

$$R_F-(CH_2)_n-X-[C_3H_5(OH)]-Y-(CH_2)_m-R'_F \quad (IV)$$

in which $C_3H_5(OH)$ represents the structures:

$$-CH_2-\underset{\underset{OH}{|}}{CH}-CH_2- \quad \text{or} \quad -\underset{\underset{CH_2OH}{|}}{CH}-CH_2- \quad \text{or}$$

$$-CH_2-\underset{\underset{CH_2OH}{|}}{CH}-$$

$R_F$ and $R'_F$, which are identical or different, represent a linear or branched perfluorinated $C_4$–$C_{20}$ alkyl radical or a mixture of linear or branched perfluorinated $C_4$–$C_{20}$ alkyl radicals;

m and n, which are identical or different, represent 0, 1, 2, 3 or 4;

X and Y, which are identical, are —O— or —S—.

These compounds are described in DE-2,702,607, JP 89-193,236, JP 92-275,268 and U.S. Pat. No. 3,893,984.

There may also be used the compounds of formula:

$$R_F-(CH_2)_n-X-[C_3H_5(OH)]-Y-(CH_2)_m-R'_F \quad (I')$$

in which $C_3H_5(OH)$ represents the structures:

$$-CH_2-\underset{\underset{OH}{|}}{CH}-CH_2- \quad (Ia)$$

or $$-\underset{\underset{CH_2OH}{|}}{CH}-CH_2- \quad (Ib)$$

or $$-CH_2-\underset{\underset{CH_2OH}{|}}{CH}- \quad (Ic)$$

$R_F$ and $R'_F$, which are identical or different, represent a linear or branched perfluorinated $C_4$–$C_{20}$ alkyl radical or a mixture of linear or branched perfluorinated $C_4$–$C_{20}$ alkyl radicals;

m and n, which are identical or different, represent 0, 1, 2, 3 or 4 and X is O and Y is S or X is S and Y is O.

The compounds of formula (I') can be prepared using the reaction of an acidic hydrogen-containing fluorinated compound of formula (II'):

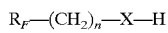

with an epoxide of formula (III'):

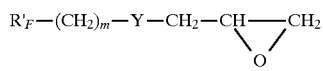

or the reaction of an acidic hydrogen-containing fluorinated compound of formula (IV'):

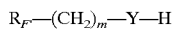

with a fluorinated epoxide of formula (V'):

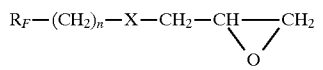

in the presence of a basic or acidic compound playing the part of reagent or catalyst. The compounds are described in FR 9,306,605.

There may also be used, according to the invention, the compounds described in the document U.S. Pat. No. 3,952,066, of formula:

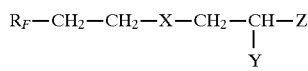

where Y is OH, and
Z is

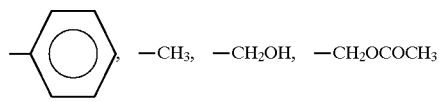

or alternatively Y is —CH$_2$OH and Z is —O—COCH$_3$
X represents

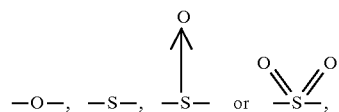

and
R$_F$ represents a linear or branched perfluorinated C$_4$–C$_{20}$ alkyl radical, or a mixture of linear or branched perfluorinated C$_4$–C$_{20}$ alkyl radicals;
or alternatively the compounds described in the document DE 2,052,579, of formula:

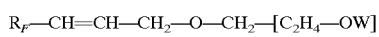

where

C$_2$H$_4$OW designates:

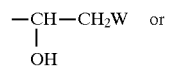 (a)

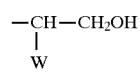 (b)

W designating:

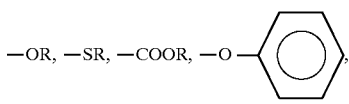

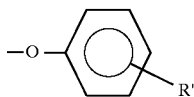

R designates a linear or branched C$_1$–C$_{18}$ alkyl radical,
R' designates —CH$_3$ or —OH, in the ortho or para position, and
R$_F$ represents a linear or branched perfluorinated C$_4$–C$_{20}$ alkyl radical, or a mixture of linear or branched perfluorinated C$_4$–C$_{20}$ alkyl radicals.

Moreover, there may be mentioned, by way of example, the products sold under the name NOFABLE FO by the company NIPPON OIL & Co, having the following formula:

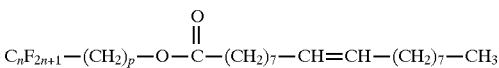

in which n is an integer equal to 6 or 8 and p is 1 or 2.

In addition to one or more fluorohydrocarbons, the continuous fatty phase may, according to the invention, contain other compounds customarily used in the cosmetic field. These may be active compounds but also compounds customarily used as excipient.

This set of additives, according to the invention, preferably does not exceed 50% by weight relative to the weight of the fatty continuous phase.

The following hydrocarbon oils and waxes may be used as additive:

- inorganic oils such as paraffin oil, vaseline oil and inorganic oils having a boiling point between 310° and 410° C.,
- oils of animal origin such as perhydrosqualene,
- vegetable oils such as sweet almond oil, sesame oil, calophyllum oil, palm oil, avocado oil, jojoba oil, olive oil, castor oil, grain germ oils such as wheat germ oil,
- synthetic esters such as Purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate and diisopropyl adipate,
- organic alcohols such as oleyl alcohol, linoleyl alcohol, linolenyl alcohol, isostearyl alcohol and octyl dodecanol,
- esters derived from lanolin acid such as isopropyl lanolate and isocetyl lanolate,
- acetylglycerides, octanoates and decanoates of alcohols and polyalcohols such as those of glycol and glycerol, ricinoleates of alcohols and polyalcohols such as that of cetyl,
- inorganic waxes such as microcrystalline waxes, paraffin, vaseline and ceresine,
- fossil waxes such as ozocerite and montan wax,
- waxes of animal origin such as bees wax, spermaceti, lanolin wax, derivatives derived from lanolin such as lanolin alcohols, hydrogenated lanolin, hydroxylated lanolin, acetylated lanolin, lanolin fatty acids, acetylated lanolin alcohol, waxes of plant origin such as candelilla wax, Carnauba wax, Japan wax and cocoa butter, synthetic waxes such as polyethylene waxes, hydrogenated oils which are solid at 25° C. such as hydrogenated castor oil, hydrogenated palm oil, hydrogenated tallow and hydrogenated coconut oil, fatty esters which are solid at 25° C. such as propylene glycol monomyristate and myristyl myristate, among the waxes, there may also be mentioned: cetyl alcohol, stearyl alcohol, mono-, di- and triglycerides which are solid at 25° C., stearoyl monoethanolamide, rosin and its derivatives such as abietates of glycol and glycerol, sucroglycerides and oleates, myristates, lanolates, stearates and dihydroxystearates of calcium, magnesium, zinc and aluminium.

There may also be mentioned the following silicone compounds:

cyclic dimethylpolysiloxanes, low and/or high viscosity dimethylpolysiloxanes, silicone gums, organopolysiloxanes such as phenylmethylpolysiloxanes and phenyltrimethylsiloxypolysiloxanes, alkylmethylpolysiloxanes, alkoxymethylpolysiloxanes, silicones containing functional groups such as alcohol or amine or thiol functional groups.

Moreover, the following perfluorinated oils may also be mentioned:

oils belonging to the group of perfluoroalkanes, perfluorocycloalkanes, perfluoropolycycloalkanes and perfluoro(alkylcycloalkanes), but also those belonging to the group of aromatic perfluorinated hydrocarbons or alternatively those belonging to the group of perfluorinated hydrocarbons containing at least one heteroatom such as tertiary amines, saturated heterocyclic compounds or finally perfluoropolyethers.

There may also be incorporated into the continuous fatty phase oily gelling agents such as for example:

metallic esters such as polyoxyaluminium stearate or aluminium and magnesium hydroxystearate, esters of fatty acids and of glycol and triglycerides, mixtures of fatty alcohols, derivatives of cholesterol especially hydroxycholesterol, clayey minerals which swell with oils belonging to the group of montmorillonites.

The continuous fatty phase may, in addition, contain screening agents, vitamins, hormones, antioxidants, preservatives, colorants, perfumes and any lipophilic additive customarily used in cosmetics.

As regards the aqueous phase of the emulsion according to the invention, it represents 10 to 90% by weight of the total formula of the emulsion.

The aqueous phase may contain, in addition to water, a certain number of other water-soluble constituents which are often used in the cosmetics field, such as, polyols such as propylene glycol, 1,3-butylene glycol, glycerol, polyglycerol, sorbitol, glucose or alternatively sucrose, in proportions not exceeding 80% by weight relative to the aqueous phase, aqueous gelling agents such as:

polysaccharides such as cellulosic derivatives (carboxymethylcellulose, hydroxypropyl methylcellulose and the like) and also xanthan or carob gum, proteins such as sulphonic keratin, collagen or elastin, silicates such as aluminium and magnesium silicate, acrylic derivatives such as carbomers and glycerol polyacrylate, polyethylene glycols, active ingredients such as sodium hyaluronate, sodium salt of pyroglutamic acid, magnesium gluconate, trace elements and biological derivatives, glyceryl polymethacrylate, salts such as magnesium sulphate or sodium chloride, clayey minerals which swell in aqueous medium, such as saponite, hectorite or alternatively smectite, amino acids, colorants.

According to the invention, the aqueous phase is emulsified with a silicone surfactant of the following general formula (II):

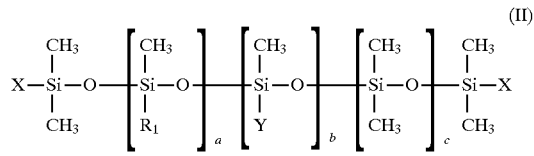

in which:

X represents $CH_3$, $(CH_2)_p$—$(C_2H_4O)_m$—$(C_3H_6O)_n$—$R_2$

Y represents $(CH_2)_p$—O—$(C_2H_4O)_n$—$(C_3H_6O)_n$—$R_2$ $R_1$ represents a $C_2$–$C_{18}$ alkyl radical $R_2$ represents H, a $C_1$–$C_5$ alkyl radical, an aryl radical or an acetyl radical, p=1 to 5 m=0 to 50 n=0 to 30, m and n not simultaneously being 0 a=0 to 100 b=1 to 50 c=0 to 300.

Preferably, in this formula (II), a and c are not simultaneously zero.

Such surfactants are commercial products and there may be mentioned by way of example, among alkyldimethicone copolyols, that is to say the compounds where a is not zero, the compounds sold under the names:

"ABIL WS 08", "ABIL WE 09", "ABIL EM 90" by the company GOLDSCHMIDT,

"Q2 5200" by the company DOW CORNING, and

"218-1138" by the company GENERAL ELECTRIC.

Among the dimethicone copolyols, that is to say the compounds for which a is zero, there may be mentioned especially the compounds sold under the names:

"KF 6015", "KF 6017", "X 224013" by the company SHIN ETSU CHEMICAL,

"SLM 55033" by the company WACKER, and

"Q2-3225 C" by the company DOW CORNING.

Also by way of example, there may be mentioned the silicone surfactants of the following formula (VIII):

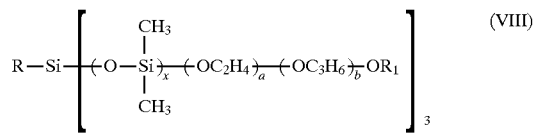

where R and $R_1$ are $C_1$ to $C_8$ alkyl groups, a and b have a value between 0 and 200, a and b not simultaneously being zero and x has a value between 1 and 100.

Preferably, a and b have a value between 0 and 50.

Among the compounds of this type, there may be mentioned the compounds marketed by the company UNION CARBIDE under the names "SILWET L-720" and "SILWET L-722".

According to the invention, these silicone surfactants are used in proportions of between 0.5 and 40% by weight relative to the weight of the emulsion. Preferably, these proportions are between 2 and 10% by weight.

When the dimethicone copolyols are used, they are preferably used in combination with at least one hydrocarbon surfactant whose HLB (hydrophilic lipophilic balance) is less than 7. In this case, the hydrocarbon surfactant is used in proportions ranging from 0 to 5% by weight relative to the total weight of the emulsion.

By way of example, among the customary hydrocarbon surfactants, there may be mentioned metallic salts of fatty acids such as magnesium lanolate, esters of fatty acid and of glycerol, of polyglycerol or alternatively of sorbitol such as oleic acid monoglyceride, polyglyceryl diisostearate or sorbitan monoisostearate, and esters of sucrose such as sucrose distearate.

Moreover, the emulsions of the invention may contain pulverulent products, in proportions of between 0 and 95% by weight relative to the weight of the emulsion. By way of example, among the pulverulent products of natural or synthetic origin, there may be mentioned vegetable powders such as maize, wheat or rice starch, mineral powders such as talc, kaolin, mica, silica, silicates, alumina, zeolites, hydroxyapatite, sericite, titanium dioxide, mica-titanium, zinc oxide, barium sulphate, iron oxides, manganese violet, chromium oxide, ultramarine blue and bismuth oxychloride, or alternatively boron nitride, metallic powders such as aluminium powder, organic powders such as nylon powders, polyamide powders, polyester powders, cellulose powders, polyethylene powders, polypropylene powders, polystyrene powders, polytetrafluoroethylene powders and organometallic pigments combining zirconium, barium or aluminium with organic colorants.

These pulverulent products which are mentioned may optionally be coated with metallic salts of fatty acids, with amino acids, lecithin, collagen, polyethylene, silicone compounds, fluorinated compounds, fluorosilicone compounds or any other customary coating.

To prepare the emulsions of the invention, a customary procedure similar to that for conventional or silicone W/O emulsions, is followed.

Another subject of the invention consists of the use of the silicone surfactants of formula (II) or (VIII) for the preparation of the emulsions according to the invention.

Another subject of the invention consists of a process for preparing a W/O type emulsion containing an aqueous phase emulsified by a silicone surfactant, in a continuous fatty phase containing at least one fluorohydrocarbon, characterized in that the surfactant is solubilized or dispersed in the fatty phase, and the aqueous phase is incorporated into the mixture with stirring.

The fluorohydrocarbons of the invention may be provided, in the pure state, in various physical forms, that is to say that they may be liquid, pasty or alternatively solid. To prepare the emulsion, the various constituents of the fatty phase are weighed together or separately. They are then heated to a temperature where they are all in the liquid state or solubilized and then mixed.

Moreover, the surfactant(s) are then solubilized or dispersed, with the use of heat, in the fatty phase.

When pulverulent products are expected in the fatty phase, they are, in this case, incorporated therein.

The aqueous phase is incorporated, with vigorous stirring, into the fatty phase and the emulsion may then be subsequently cooled to room temperature, preferably gradually and while maintaining the stirring.

The emulsions obtained, at room temperature, may be provided in various physical forms. The physical form of the emulsions obtained is linked to the nature of the constituents present in each of the phases, aqueous phase and fatty continuous phase, as well as to the respective proportion of one phase relative to the other.

The emulsions thus obtained are stable for several months within a broad range of temperatures of between $-4°$ and $+45°$ C. and they withstand the test of centrifugation of 4000 rpm for one hour.

Moreover, in addition to the fact, mentioned above, that emulsions can be prepared for a very broad range of value of the substitution rate, it appeared that emulsions according to the invention can be prepared for broad ranges of water content of the emulsion.

Thus, in a manner similar to the emulsions where the continuous phase is hydrocarbon-containing or silicone, it is possible to obtain emulsions of very different viscosity ranging from very fluid to the solid state by varying the percentage of aqueous phase and/or by choosing the gelling or structuring constituents in each of the phases.

In order to produce the W/O type emulsion, the continuous phase containing the fluorohydrocarbon should not be miscible with the aqueous phase. Thus, the fluorohydrocarbon should not be water-soluble.

Similarly, the adjustment of the refractive indices between the fatty phase and the aqueous phase by the addition of polyols into the latter makes it possible to obtain transparent emulsions and the higher the level of fluorine in the fatty phase, the lower the percentage of polyols.

These emulsions contain, moreover, good sensory properties linked to the presence of the fluoro-hydrocarbons: they are indeed comfortable, very easy to apply and result in the formation of a film which is very thin, very smooth, very uniform and meeting the protection and behaviour requirements.

Given these properties and the broad range of emulsions which can be obtained according to the invention, the applications of the emulsions according to the invention in the cosmetics and dermatological field are many. These applications relate both to white products and to coloured products. These emulsions according to the invention may be provided in the form of a milk, a cream for skin or hair care, anti-sun cream, coloured cream, foundation, lipstick, mascara or blusher.

The emulsions of the invention or the cosmetic compositions prepared with these emulsions can therefore be used for the treatment or care of the skin, the hair or the nails.

Other characteristics and advantages of the invention will emerge on reading the examples below and which are intended to illustrate the invention without limiting its scope.

Examples of preparation of fluorohydrocarbon surfactants.

EXAMPLE I 1-(2'-F-Hexylethylthio)-3-(2"-ethylhexyloxy)-2-propanol In the Presence of Sodium Methoxide 3.6 g of a methanolic solution of sodium methoxide (about 30%–5.54 meq $g^{-1}$) are added to 152 g of 2-F-hexylethanethiol, over one minute, at the temperature of 25° C., with stirring and under a nitrogen stream.

The mixture is heated to 70° C. The methanol present in the medium is evaporated under vacuum.

2-Ethylhexylglycidyl ether (74.4 g) is then added dropwise over one hour. The temperature of the mixture is maintained between 60° and 70° C. during the addition of the epoxide.

At the end of the addition, the temperature is adjusted to 25° C.

The mixture is neutralized by means of 20 ml of Normal HCl.

The 1-(2'-F-hexylethylthio)-3-(2"-ethylhexyloxy)-2-propanol is separated by distillation: b.p.=141° C./66.5 Pa.

175 g (77%) of a colourless translucent oil are obtained.

| Elemental analysis: | % C | % H | % S | % F |
|---|---|---|---|---|
| Calculated | 40.28 | 4.80 | 5.66 | 43.60 |
| Measured | 40.37 | 4.82 | 5.55 | 43.74 |

EXAMPLE II 1-(2'-F-Octylethylthio)-3-butyloxy-2-propanol

Using the procedure described in Example 1, 40 g (0.31 mol) of butyl glycidyl ether are condensed, over 1 hour, with 147.7 g (0.31 mol) of 2-F-octylethanethiol, in the presence of 2.75 g of a methanolic solution of sodium methoxide (5.54 meq g$^{-1}$). At the end of the reaction, the mixture is neutralized with 15.5 ml of Normal HCl.

After distillation (138°–142° C./6.65 Pa), 153 g of 1-(2'-F-octylethylthio)-3-butyloxy-2-propanol are obtained in the form of a colourless oil.

Yield: 80%.

| Elemental analysis: | % C | % H | % S | % F |
|---|---|---|---|---|
| Calculated | 33.45 | 3.14 | 5.25 | 52.92 |
| Measured | 33.52 | 3.23 | 5.14 | 52.67 |

EXAMPLE III 1-(2'-F-Hexylethylthio)-3-(2'-F-hexylethoxy)-2-propanol 1.33 g of a methanolic solution of sodium methoxide (about 30%–5.65 meq g$^{-1}$) are added to 57 g of 2-F-hexylethanethiol, over one minute, at the temperature of 25° C., with stirring and under a nitrogen stream.

The mixture is heated to 70° C. The methanol present in the medium is evaporated under vacuum.

2-F-Hexylethylglycidyl ether (63 g–0.15 mol) is then added dropwise over one hour. The temperature of the mixture is maintained between 60° and 70° C. during the addition of the epoxide.

At the end of the addition, the temperature is adjusted to 25° C.

The mixture is neutralized by means of 7.5 ml of Normal HCl.

The 1-(2'-F-hexylethylthio)-3-(2'-F-hexylethoxy)-2-propanol is separated by distillation: b.p.=170° C./133 Pa.

85 g (71%) of a colourless translucent oil are obtained.

| Elemental analysis: | % C | % H | % S | % F |
|---|---|---|---|---|
| Calculated | 28.51 | 1.76 | 4.01 | 61.72 |
| Measured | 28.60 | 1.79 | 4.32 | 61.54 |

EXAMPLE IV 1-(2'-F-Hexylethylthio)-3-octylthio-2-propanol 0.61 g of a methanolic solution of sodium methoxide (about 30%–5.65 meq g$^{-1}$) is added to 10.05 g (0.069 mol) of octanethiol, at the temperature of 25° C., under a nitrogen stream.

The mixture is heated to 70° C. The methanol present in the medium is evaporated under vacuum.

2-F-Hexylethylthioglycidyl ether (30 g –0.069 mol) is then added dropwise over 30 minutes. The temperature of the mixture is maintained between 60° and 70° C. during the addition of the epoxide.

At the end of the addition, the temperature is adjusted to 25° C.

The mixture is neutralized by means of 3.5 ml of Normal HCl.

The 1-(2'-F-hexylethylthio)-3-octylthio-2-propanol is separated by distillation: b.p.=178° C./66.5 Pa.

30 g (75%) of a colourless transparent oil are obtained.

| Elemental analysis: | % C | % H | % S | % F |
|---|---|---|---|---|
| Calculated | 39.18 | 4.67 | 11.01 | 42.40 |
| Measured | 39.16 | 4.65 | 10.57 | 42.46 |

Examples of Preparation of Emulsions

EXAMPLES 1 to 9 (2, 4, 6, 8 Comparative)

Emulsions are obtained in the following manner:

10.0 g of surfactant are solubilized or dispersed in 20.0 g of fluorohydrocarbon at a temperature of 70° C. Then, 70.0 g of water are added slowly, with stirring, while maintaining during the addition a minimum temperature of 50° C. The mixture is then allowed to return gradually to room temperature while maintaining the stirring.

The following surfactants are used:

Hydrocarbon surfactant (HS) (Examples 4, 8) Isostearyl diglyceryl succinate sold under the name "IMWITOR 780 K" by the company HULS FRANCE Silicone surfactant (SS) (Examples 1, 3, 5, 7, 9) Cetyldimethicone copolyol sold under the name "ABIL EM 90" by the company GOLDSCHMIDT Fluorinated surfactant (FS) (Examples 2, 6) $C_6F_{13}$—$C_2H_4$—S—$C_2H_4O(C_2H_4O)_2$—H described in FR 2,565,226.

The following fluorohydrocarbons are used:

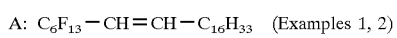

A: $C_6F_{13}$—CH=CH—$C_{16}H_{33}$ (Examples 1, 2)

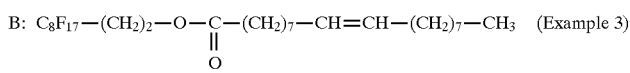

B: $C_8F_{17}$—$(CH_2)_2$—O—C—$(CH_2)_7$—CH=CH—$(CH_2)_7$—$CH_3$ (Example 3)
∥
O

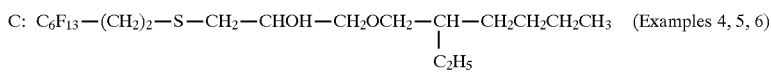

C: $C_6F_{13}$—$(CH_2)_2$—S—$CH_2$—CHOH—$CH_2OCH_2$—CH—$CH_2CH_2CH_2CH_3$ (Examples 4, 5, 6)
|
$C_2H_5$ -continued
D: $C_8F_{17}-(CH_2)_2-S-CH_2-CHOH-CH_2O-CH_2CH_2CH_2CH_3$ (Example 7)
E: $C_6F_{13}-CH=CH_2$ (Examples 8, 9)
F: $C_6F_{13}-(CH_2)_2-S-CH_2-CHOH-CH_2-O(CH_2)_2C_6F_{13}$
G: $C_6F_{13}-(CH_2)_2-S-CH_2-CHOH-CH_2-S-C_8H_{17}$
I: $C_6F_{13}-(CH_2)_2-O-CH_2-CHOH-CH_2-O-(CH_2)_2-CH_2-\underset{\underset{C_2H_5}{|}}{CH}-C_4H_9$ The emulsions obtained are examined and the results appear in Table I below.

TABLE I

| FLUOROHYDROCARBON | % F | EXAMPLES | | |
|---|---|---|---|---|
| | | HS | SS | FS |
| A | 27.1 | | 1 +++ | 2 -- |
| B | 31.5 | | 3 +++ | |
| C | 33.3 | 4 - | 5 +++ | 6 -- |
| D | 48.5 | | 7 ++ | |
| E | 81.3 | 8 - | 9 + | |
| F | 66.7 | | ++ | -- |
| G | 33.3 | | +++ | |
| I | 33.3 | | +++ | |

+++Stable, very fine to fine emulsion
++Stable, average emulsion
+Stable, fairly coarse emulsion
-Unstable, coarse emulsion
--Very unstable emulsion, rapid separation into two phases.

EXAMPLES 10 TO 15 (4, 6, 10, 12, 13, 15 Comparative)

The emulsions are prepared according to the procedure described for Examples 1 to 9, from 1-(2'-F-hexylethylthio)-3-(2''-ethylhexyloxy)-2-propanol, fluorohydrocarbon C of formula:

$$C_6F_{13}-(CH_2)_2-S-CH_2-CHOH-CH_2-O-CH_2-\underset{\underset{CH_2-CH_3}{|}}{CH}-(CH_2)_3-CH_3$$

The surfactants used for Examples 1 to 9, where they are designated by HS, SS and FS, are used.

The emulsions obtained are examined and the results appear in Table II below.

TABLE II

| % S | % Water | % Fluoro-hydrocarbon | HS | SS | FS |
|---|---|---|---|---|---|
| 40 | 10 | 50 | (10) -- | (11) ++ | (12) -- |
| 10 | 70 | 20 | (4) -- | (5) +++ | (6) -- |
| 5 | 85 | 10 | (13) -- | (14) +++ | (15) -- | where the numbers indicated in brackets represent the numbers for the examples.

EXAMPLES 16 TO 19

Emulsions are obtained in the following manner:

3.0 g of the surfactant SS, defined in the examples above, are solubilized in a solution of 15.0 g of the fluorohydrocarbon C defined in Examples 10 to 15 and 15.0 g of each of the oils $H_1$ to $H_4$ represented in Table III below, at a temperature of 60° C.

67.0 g of water are then added slowly, with stirring, while maintaining during the addition a minimum temperature of 50° C. The mixture is then allowed to return to room temperature while maintaining the stirring.

The emulsions obtained are examined and the results appear in Table III below.

TABLE III

| OIL | EXAMPLE | QUALITY OF THE EMULSION |
|---|---|---|
| H1 Jojoba oil | 16 | +++ |
| H2 Hydrogenated isoparaffin | 17 | +++ |
| H3 Cyclopenta-dimethylsiloxane | 18 | +++ |
| H4 Perfluoro-decalin | 19 | ++ |

EXAMPLE 20

3.0 g of the surfactant SS defined above are solubilized in 30.0 g of the fluorohydrocarbon C, at a temperature of 70° C.

A mixture of 34.0 g of glycerol with 33.0 g of water are then added slowly, with stirring, while maintaining during the addition a minimum temperature of 50° C.

The mixture is then allowed to return to room temperature while maintaining the stirring.

A transparent emulsion is then obtained.

EXAMPLE 21

3.0 g of the surfactant SS defined above are solubilized in 30.0 g of the fluorohydrocarbon C, at a temperature of 70° C.

A mixture of 29.1 g of hexaglycerol sold under the name "Polyglycerine 500" by the company SAKAMOTO YAKU-HIN and 37.9 g of water are then added slowly, with stirring, while maintaining during the addition a minimum temperature of 50° C.

The mixture is then allowed to return to room temperature while maintaining the stirring.

A transparent emulsion is then obtained.

EXAMPLE 22

10.0 g of lauryldimethicone copolyol sold under the name "Q2-5200" by the company DOW CORNING are solubilized in 20.0 g of the fluorohydrocarbon C at a temperature of 70° C.

Then, 70.0 g of water are added slowly, with stirring, while maintaining during the addition a minimum temperature of 50° C.

The mixture is then allowed to return gradually to room temperature while maintaining the stirring.

A fine and stable emulsion is then obtained.

EXAMPLE 23

10.0 g of decyldimethicone copolyol sold under the name "218-1138" by the company GENERAL ELECTRIC are solubilized in 20.0 g of the fluorohydrocarbon C.

Then, 70.0 g of water are added slowly, with stirring, while maintaining during the addition a minimum temperature of 50° C.

The mixture is then allowed to return gradually to room temperature while maintaining the stirring.

A fine and stable emulsion is then obtained.

EXAMPLE 24

A mixture of 2.5 g of dimethicone copolyol sold under the name "KF 60-17" by the company SHIN-ETSU CHEMICAL and 2.5 g of HS is solubilized in 25.0 g of fluorohydrocarbon C at a temperature of 70° C.

Then, 70.0 g of water are added slowly, with stirring, while maintaining during the addition a minimum temperature of 50° C.

The mixture is then allowed to return gradually to room temperature while maintaining the stirring.

A fine and stable emulsion is thus obtained.

EXAMPLE 25

A mixture of 2.5 g of dimethicone copolyol, sold under the name "SILWET L-722" by the company UNION CARBIDE and 2.5 g of HS is solubilized in 25 g of fluorohydrocarbon C at a temperature of 70° C.

Then, 70 g of water are added slowly, with stirring, while maintaining during the addition a minimum temperature of 50° C.

The mixture is then allowed to return to room temperature while maintaining the stirring.

A fine and stable emulsion is then obtained.

EXAMPLE 26

White Cream Constituents

|  | % |
|---|---|
| Phase H | |
| 1-(2'-F-Hexylethylthio)-3-(2"-ethylhexyloxy)-2-propanol | 29.40 |
| Cetyldimethicone copolyol, sold under the name "Abil EM 90" by the company GOLDSCHMIDT | 3.00 |
| Glycoldistearate + tristearin, sold under the name "UNITWIX" by the company GUARDIAN | 0.50 |
| Propylparaben | 0.10 |
| Phase E | |
| Water | 61.10 |
| Magnesium sulphate | 0.70 |
| Glycerol | 5.00 |
| Methylparaben | 0.20 |
|  | 100.00 |

Procedure

The compounds of phase H are weighed together and then heated to 70° C. The constituents of phase E are also weighed together and then heated to 80° C.

After homogenization of the two phases, phase E is added slowly to phase H while stirring by means of a Moritz type stirrer at a speed of 4000 rpm and while maintaining during the addition a minimum temperature of 50° C.

The mixture is then allowed to return gradually to room temperature while maintaining the stirring.

A white cream is obtained which is distinguishable by good spreading and penetrating properties resulting in the formation of a very smooth film on the skin.

EXAMPLE 27

White Cream Constituents

| Phase H | % |
|---|---|
| Phase H | |
| 1-(2'-F-Hexylethylthio-3-(2"-ethylhexyloxy)-2-propanol | 29.40 |
| Laurylmethicone copolyol, sold under the name "Q2-5200" by the company DOW CORNING | 5.00 |
| Glycoldistearate + tristearin, sold under the name "UNITWIX" by the company GUARDIAN | 0.50 |
| Propylparaben | 0.10 |
| Phase E | |
| Water | 59.10 |
| Magnesium sulphate | 0.70 |
| Glycerol | 5.00 |
| Methylparaben | 0.20 |
|  | 100.00 |

The procedure is the same as that which is described in Example 26.

EXAMPLE 28

White Cream Constituents

| Phase H | % |
|---|---|
| 1-(2'-F-Octylethylthio)-3-butyloxy-2-propanol | 29.40 |
| Cetyldimethicone copolyol, sold under the name "ABIL EM 90" by the company GOLDSCHMIDT | 3.00 |
| Glycoldistearate + tristearin, sold under the name "UNITWIX" by the company GUARDIAN | 0.50 |
| Propylparaben | 0.10 |
| Phase E | |
| Water | 61.10 |
| Magnesium sulphate | 0.70 |
| Glycerol | 5.00 |
| Methylparaben | 0.20 |
|  | 100.00 |

The procedure is the same as that described in Example 26.

EXAMPLE 29

Anti-Sun Cream Constituents

|  | % |
|---|---|
| Phase H | |
| 1-(2'-F-Hexylethylthio)-3-(2"-ethylhexyloxy)-2-propanol | 12.00 |
| Cetyldimethicone copolyol, sold under the name "Abil EM 90" by the company GOLDSCHMIDT | 3.00 |
| Glycoldistearate + tristearin, sold under the name "UNITWIX" by the company GUARDIAN | 0.50 |
| Octylmethoxycinnamate, sold under the name "PARSOL MCX" by the company GIVAUDAN ROURE | 5.00 |
| Propylparaben | 0.10 |
| Silicone compound S | |
| Cyclopentadimethylsiloxane | 6.40 |
| Phase E | |
| Water | 67.20 |
| Magnesium sulphate | 0.70 |
| Glycerol | 5.00 |
| Methylparaben | 0.10 |
|  | 100.00 |

Procedure

The compounds of phase H are weighed together and heated to 70° C.

After homogenization, the phase is cooled to 60° C. and then the compound S is added.

After homogenization, the phase E, previously heated to 80° C., is added slowly and then cooled to 50° C. while stirring by means of a Moritz type stirrer and while maintaining during the addition a minimum temperature of 50° C.

The mixture is then allowed to return gradually to room temperature while maintaining the stirring.

An anti-sun cream is obtained which is distinguishable by good spreading properties, resulting in the formation of a film which is very protective and very smooth on the skin.

In the following examples where pigments are used, they are defined below, with their name:

| Silicone coating: | |
|---|---|
| Yellow iron oxide: | "W1802 COVASIL 3.05" |
| Red iron oxide: | "W3801 COVASIL 3.05" |
| Black iron oxide: | "W9814 COVASIL 3.05" |
| Titanium dioxide: | "W877 COVASIL 05" |
| Fluorinated coating: | |
| Yellow iron oxide: | "COVAFLUOR" |
| Red iron oxide: | "COVAFLUOR" |
| Black iron oxide: | "COVAFLUOR" |
| Titanium dioxide: | "COVAFLUOR" |

The pigments with coating are marketed in France by WACKHERR.

EXAMPLE 30

Foundation Constituents

|  | % |
|---|---|
| 1-(2'-F-Octylethylthio)-3-ethylhexylexy-2-propanol | 29.40 |
| Cetyldimethicone copolyol, sold under the name "ABIL EM 90" by the company GOLDSCHMIDT | 3.00 |
| Glycoldistearate + Tristearin, sold under the name "UNITWIX" by the company GUARDIAN | 0.50 |
| Propylparaben | 0.10 |
| Phase E | |
| Water | 57.20 |
| Magnesium sulphate | 0.70 |
| Glycerol | 5.00 |
| Methylparaben | 0.10 |
| Pigment | |
| Yellow iron oxide with silicone coating | 0.60 |
| Red iron oxide with silicone coating | 0.39 |
| Black iron oxide with silicone coating | 0.11 |
| Titanium dioxide with silicone coating | 2.90 |
|  | 100.00 |

Procedure

The compounds of the phase H are weighed together and then heated to 70° C. The constituents of the phase E are also weighed together and then heated to 80° C.

The pigments are dispersed in the phase H while stirring by means of a Moritz type stirrer, and then, after homogenization, the phase E is added slowly while maintaining the stirring and while maintaining during the addition a minimum temperature of 50° C.

The mixture is then allowed to return gradually to room temperature while maintaining the stirring.

A pink beige foundation is obtained which spreads well, which results in a very natural and very smooth make-up, and which has a good cosmetic behaviour.

EXAMPLE 31

Foundation Constituents

|  | % |
|---|---|
| Phase H | |
| 1-(2'-F-Hexylethylthio)-3-(2"-ethylhexyloxy)-2-propanol | 29.40 |
| Cetyldimethicone copolyol, sold under the name "ABIL EM 90" by the company GOLDSCHMIDT | 3.00 |
| Glycoldistearate + Tristearin, sold under the name "UNITWIX" by the company GUARDIAN | 0.50 |
| Propylparaben | 0.10 |
| Phase E | |
| Water | 57.20 |
| Magnesium sulphate | 0.70 |
| Glycerol | 5.00 |
| Methylparaben | 0.10 |
| Pigments | |
| Yellow iron oxide with fluorinated coating | 0.60 |
| Red iron oxide with fluorinated coating | 0.39 |
| Black iron oxide with fluorinated coating | 0.11 |
| Titanium dioxide with fluorinated coating | 2.90 |
|  | 100.00 |

EXAMPLE 32

Foundation Constituents

| | % |
|---|---|
| Phase H | |
| 1-(2'-F-Hexylethylthio)-3-(2"-ethylhexyloxy)- 2-propanol | 12.00 |
| Cetyldimethicone copolyol, sold under the name "ABIL EM 90" by the company GOLDSCHMIDT | 3.00 |
| Glycoldistearate + Tristearin, sold under the name "UNITWIX" by the company GUARDIAN | 0.50 |
| Propylparaben | 0.10 |
| Silicone compound S | |
| Cyclopentadimethylsiloxane | 11.40 |
| Pigments | |
| Yellow iron oxide with silicone coating | 0.60 |
| Red iron oxide with silicone coating | 0.39 |
| Black iron oxide with silicone coating | 0.11 |
| Titanium dioxide with silicone coating | 2.90 |
| Phase E | |
| Water | 63.20 |
| Magnesium sulphate | 0.70 |
| Glycerol | 5.00 |
| Methylparaben | 0.10 |
| | 100.00 |

Procedure

The compounds of the phase H are weighed together and heated to 70° C.

After homogenization the phase is cooled to 60° C. and then the silicone compound S is added.

The pigments P are then dispersed in the H+S mixture. After homogenization, the phase E, previously heated to 80° C. and then cooled to 50° C., is added slowly, while stirring by means of a Moritz type stirrer and while maintaining during the addition a minimum temperature of 50° C.

The mixture is then allowed to return gradually to room temperature while maintaining the stirring.

A foundation is obtained which has the same characteristics as the ones above.

EXAMPLE 33

Foundation Constituents

| | % |
|---|---|
| Phase H | |
| 1-(2'-F-Hexylethylthio)-3-(2"-ethylhexyloxy)- 2-propanol | 12.00 |
| Cetyldimethicone copolyol, sold under the name "ABIL WE09" by the company GOLDSCHMIDT | 3.00 |
| Propylparaben | 0.10 |
| Silicone compound S | |
| Bentone sold under the name "SIMAGEL SI-345" by the company STEARINERIES DUBOIS | 1.00 |
| Cyclopentadimethylsiloxane | 10.90 |

-continued

| | % |
|---|---|
| Pigment P | |
| Yellow iron oxide coated with Teflon (T-9533 from WARNER-JENKINSON) | 0.60 |
| Red iron oxide coated with Teflon (T-9555 from WARNER-JENKINSON) | 0.39 |
| Black iron oxide coated with Teflon (T-9560 from WARNER-JENKINSON) | 0.11 |
| Titanium dioxide coated with Teflon (T-9528 from WARNER-JENKINSON) | 2.90 |
| Phase E | |
| Water | 62.20 |
| Magnesium sulphate | 0.70 |
| Glycerol | 5.00 |
| Methylparaben | 0.10 |
| | 100.00 |

The procedure is carried out according to the procedure of Example 30.

We claim:

1. Cosmetic or dermatological emulsion of the water-in-oil type, comprising an aqueous phase emulsified by means of a silicone surfactant in a continuous fatty phase containing at least one fluorohydrocarbon, wherein said fluorohydrocarbon is liquid, solid or pasty, has a substitution ratio of between 0.5 and 95%, has at least one hydrocarbon group and has the formula (I):

$$(R_F)_x \text{—} (A)_y \text{—} (R_H)_z \qquad (I)$$

in which:

x represents 1, 2 or 3, y represents 0 or 1, z represents 0, 1, 2 or 3, on the condition that y and z are not simultaneously 0, and that when z is 0, x is 2 or 3, $R_F$ represents a fluorinated radical selected from the group consisting of saturated and unsaturated, linear, branched and cyclic, aliphatic and aromatic fluorinated radicals which may be functionalized by insertion, terminal or pendant substitution of the backbone by at least one organic functional group selected from the group consisting of an alcohol, thiol, acid, carbonyl, sulfoxide, ester, amide, amine, phosphate, ethylene, acetylene, enamide and sulfonamide, interrupted by one or more oxygen or sulfur atoms or carrying hydrogen substituents or halogen substituents other than fluorine, provided that for any two carbon atoms of the skeleton, no more than one of said substituents other than fluorine is present on said two carbon atoms, $R_H$ is an aliphatic hydrocarbon radical selected from the group consisting of saturated and unsaturated, linear and branched radicals, which may be functionalized by insertion, terminal or pendant substitution of the backbone by at least one organic functional group selected from the group consisting of an alcohol, thiol, acid, carbonyl, sulfoxide, ester, amide, amine, phosphate, ethylene, acetylene, enamide and sulfonamide, or interrupted by one or more oxygen or sulfur atoms, A represents a di-, tri- or quadrivalent radical of the formula:

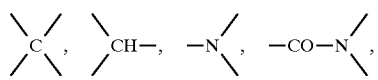 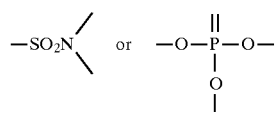

or cyclic, aliphatic or aromatic structures or ethylenic unsaturations; the aqueous phase representing 10 to 90% by weight of the emulsion and said emulsion being in the form of a milk, a cream for skin or hair care, anti-sun cream, coloured cream, foundation, lipstick, mascara or blusher.

2. Emulsion according to one of claim 1, wherein the formula for the fluorohydrocarbon is the following formula (III):

$$R_1-(CH_2)_n-X-(C_3H_5(OH))-(Y)_x-R_2 \quad (III)$$

where $C_3H_5(OH)$ represents:

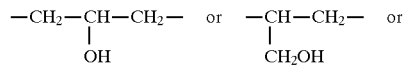
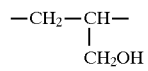

$R_1$ represents a linear or branched perfluorinated $C_4$–$C_{20}$ alkyl radical or a mixture of linear or branched perfluorinated $C_4$–$C_{20}$ radicals, $R_2$ represents a linear or branched $C_1$–$C_{22}$ alkyl radical or a mixture of linear or branched $C_1$–$C_{22}$ alkyl radicals or a $C_6$–$C_{10}$ aryl or $C_7$–$C_{15}$ aralkyl radical, X and Y, which are identical or different, represent:

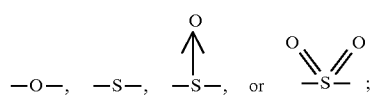

provided that X and Y do not simultaneously represent

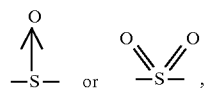

n is between 0 and 4, and
x represents 0 or 1
or the formula (IV):

$$R_F-(CH_2)_n-X-(C_3H_5(OH))-Y-(CH_2)_m-R'_F \quad (IV)$$

in which $C_3H_5(OH)$ represents the structures:

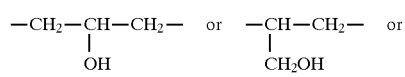

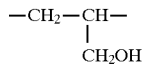

$-CH_2-CH-$
$\quad\quad |$
$\quad\quad CH_2OH$ $R_F$ and $R'_F$, which are identical or different, represent a linear or branched perfluorinated $C_4$–$C_{20}$ alkyl radical or a mixture of linear or branched perfluorinated $C_4$–$C_{20}$ alkyl radicals;

m and n, which are identical or different, represent 0, 1, 2, 3 or 4;

X and Y, which are identical, are —O— or —S—;

or the formula (I')

$$R_F-(CH_2)_n-X-(C_3H_5(OH))-Y-(CH_2)_m-R'_F \quad (I')$$

in which $C_3H_5(OH)$ represents the structures:

$-CH_2-CH-CH_2-$ (Ia)
$\quad\quad\quad |$
$\quad\quad\quad OH$ or $-CH-CH_2-$ (Ib)
$\;|$
$CH_2OH$ or $-CH_2-CH-$ (Ic)
$\quad\quad |$
$\quad\quad CH_2OH$ $R_F$ and $R'_F$, which are identical or different, represent a linear or branched perfluorinated $C_4$–$C_{20}$ alkyl radical or a mixture of linear or branched perfluorinated $C_4$–$C_{20}$ alkyl radicals;

m and n, which are identical or different, represent 0, 1, 2, 3 or 4 and X is O and Y is S or X is S and Y is O;

or the formula (V):

$$R_F-CH_2-CH_2-X-CH_2-CH-Z \quad (V)$$
$$\quad\quad\quad\quad\quad\quad\quad\quad\quad\quad\quad |$$
$$\quad\quad\quad\quad\quad\quad\quad\quad\quad\quad\quad Y$$

where Y is OH, and
Z is

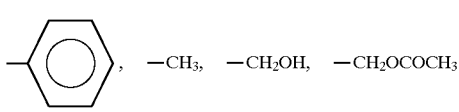

or alternatively Y is —CH$_2$OH and Z is —O—OCH$_3$
X represents

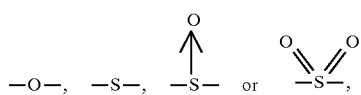

and
$R_F$ represents a linear or branched perfluorinated $C_4$–$C_{20}$ alkyl radical, or a mixture of linear or branched perfluorinated $C_4$–$C_{20}$ alkyl radicals;

or the formula (VI):

$$R_F-CH=CH-CH_2-O-CH_2-(C_2H_4-OW) \quad (VI)$$

where
$C_2H_4OW$ designates:

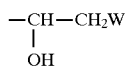

or

W designating:

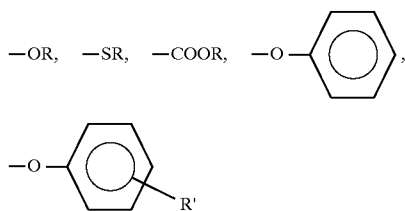

R designates a linear or branched $C_1$–$C_{18}$ alkyl radical,
R' designates —$CH_3$ or —OH, in the ortho or para position, and
$R_F$ represents a linear or branched perfluorinated $C_4$–$C_{20}$ alkyl radical, or a mixture of linear or branched perfluorinated $C_4$–$C_{20}$ alkyl radicals;
or the formula (VII):

$$C_nF_{2n+1}-(CH_2)_p-O-\overset{O}{\underset{\|}{C}}-(CH_2)_7-CH=CH-(CH_2)_7-CH_3 \quad (VII)$$

in which n is an integer equal to 6 or 8 and p is 1 or 2.

3. Emulsion according to claim 1, wherein the continuous phase contains at least 50% by weight of fluorohydrocarbon.

4. Emulsion according to claim 1, wherein the silicone surfactant is of the following formula (II):

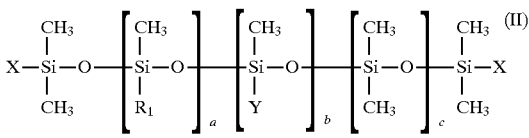

in which
X represents $CH_3$, $(CH_2)_p$—$(C_2H_4O)_m$—$(C_3H_6O)_n$—$R_2$
Y represents $(CH_2)_p$—O—$(C_2H_4O)_m$—$(C_3H_6O)_n$—$R_2$
$R_1$ represents a $C_2$–$C_{18}$ alkyl radical
$R_2$ represents H, a $C_1$–$C_5$ alkyl radical, an aryl radical or an acetyl radical,
p=1 to 5
m=0 to 50
n=0 to 30, m and n not simultaneously being 0
a=0 to 100
b=1 to 50
c=0 to 300,
or the following formula:

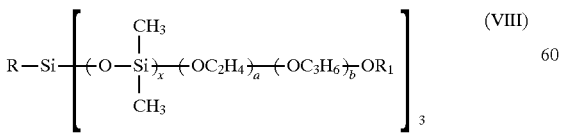

in which R and $R_1$ are $C_1$ to $C_8$ alkyl groups,
a and b have a value between 0 and 200 and x has a value between 1 and 100, a and b not simultaneously being zero.

5. Emulsion according to claim 4, wherein it comprises a silicone surfactant of formula (II) where a is zero in combination with at least one hydrocarbon surfactant with an HLB less than 7.

6. Emulsion according to claim 1, wherein the silicone surfactants are used in proportions of between 0.5 and 40% by weight relative to the weight of the emulsion.

7. Emulsion according to claim 6, wherein the silicone surfactants are used in proportions of between 2 and 10% by weight relative to the weight of the emulsion.

8. Emulsion according to claim 1, wherein it comprises, in addition, at least one pulverulent product of natural or synthetic origin.

9. Emulsion according to claim 1, which further comprises, in the fatty phase, an excipient selected from the group consisting of oils, waxes, oily gelling agents, screening agents, vitamins, hormones, antioxidants, preservatives, colorants and perfumes and, in the aqueous phase, an excipient selected from the group consisting of polyols, gelling agents, swelling agents, amino acids, colorants and active agents.

10. Emulsion according to claim 1, wherein the fluorohydrocarbons have a substitution ratio of between 10 and 80%.

11. A water-in-oil type cosmetic or dermatological emulsion comprising an aqueous phase emulsified by a silicone surfactant, in a continuous fatty phase containing at least one fluorohydrocarbon, wherein said fluorohydrocarbon has at least one hydrocarbon group, a substitution ratio of between 0.5 and 95% and is liquid, solid or pasty, and said silicone surfactant has the formula (II):

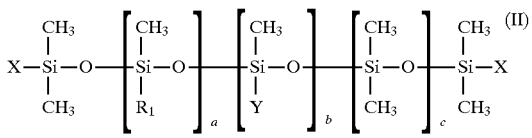

in which:
X represents $CH_3$, $(CH_2)_p$—$(C_2H_4O)_m$—$(C_3H_6O)_n$—$R_2$,
Y represents $(CH_2)_p$—O—$(C_2H_4O)_m$—$(C_3H_6O)_n$—$R_2$,
$R_1$ represents a $C_2$–$C_{18}$ alkyl radical,
$R_2$ represents H, a $C_1$–$C_5$ alkyl radical, an aryl radical or an acetyl radical,
p=1 to 5,
m=0 to 50,
n=0 to 30, m and n not simultaneously being 0,
a=0 to 100,
b=1 to 50, and
c=0 to 300
or the formula (VIII):

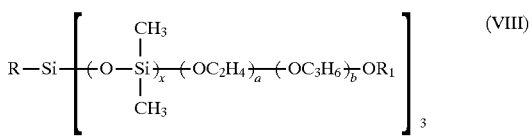

wherein R and $R_1$ are $C_1$ to $C_8$ alkyl groups, a and b have a value between 0 and 200, a and b not simultaneously being zero, and x has a value between 1 and 100;
the aqueous phase representing 10 to 90% by weight of the emulsion, said emulsion being in the form of a milk, a cream for skin or hair care, anti-sun cream, coloured cream, foundation, lipstick, mascara or blusher.

* * * * *